(12) United States Patent
Tkaczyk et al.

(10) Patent No.: US 8,824,635 B2
(45) Date of Patent: Sep. 2, 2014

(54) DETECTOR MODULES FOR IMAGING SYSTEMS AND METHODS OF MANUFACTURING

(75) Inventors: John Eric Tkaczyk, Delanson, NY (US); Kevin Matthew Durocher, Waterford, NY (US); James Rose, Guilderland, NY (US); Haochuan Jiang, Brookfield, WI (US); Abdelaziz Ikhlef, Hartland, WI (US); Vladimir Lobastov, Waterford, NY (US); Daniel David Harrison, Delanson, NY (US)

(73) Assignee: General Electric Company, Schenectady, NY (US)

( * ) Notice: Subject to any disclaimer, the term of this patent is extended or adjusted under 35 U.S.C. 154(b) by 273 days.

(21) Appl. No.: 13/283,373

(22) Filed: Oct. 27, 2011

(65) Prior Publication Data

US 2013/0108019 A1 May 2, 2013

(51) Int. Cl.
| | |
|---|---|
| H05G 1/64 | (2006.01) |
| H01L 27/148 | (2006.01) |
| G01T 1/16 | (2006.01) |
| G01T 1/208 | (2006.01) |

(52) U.S. Cl.
USPC .................. 378/98.8; 378/207; 250/363.08; 250/370.09

(58) Field of Classification Search
USPC ........ 378/19, 62, 91, 98, 98.8, 189, 204, 210; 250/252.1, 354.1, 370.01, 370.06, 250/370.08, 370.09, 370.11, 370.12, 250/370.14, 370.15, 371, 393, 395, 526
See application file for complete search history.

(56) References Cited

U.S. PATENT DOCUMENTS

| | | | | |
|---|---|---|---|---|
| 4,695,720 | A * | 9/1987 | Rieder et al. | 250/231.14 |
| 6,469,312 | B2 * | 10/2002 | Agano | 250/580 |
| 6,655,675 | B2 * | 12/2003 | Rutten et al. | 250/368 |
| 7,129,498 | B2 | 10/2006 | Hoffman | |
| 7,166,848 | B2 * | 1/2007 | El-Hanany et al. | 250/370.09 |
| 7,208,740 | B2 * | 4/2007 | El-Hanany et al. | 250/370.09 |
| 7,212,604 | B2 | 5/2007 | Tkaczyk et al. | |
| 7,289,336 | B2 | 10/2007 | Burdick et al. | |
| 7,414,248 | B1 * | 8/2008 | Kasper et al. | 250/370.08 |
| 7,450,683 | B2 | 11/2008 | Tkaczyk et al. | |
| 7,573,040 | B2 | 8/2009 | Tkaczyk et al. | |
| 7,606,346 | B2 | 10/2009 | Tkaczyk et al. | |
| 7,825,385 | B2 * | 11/2010 | Gasse et al. | 250/370.09 |
| 2007/0206721 | A1 * | 9/2007 | Tkaczyk et al. | 378/19 |
| 2010/0320556 | A1 | 12/2010 | Tredwell | |

OTHER PUBLICATIONS

Vickers et al., "Silicon-Anode Detector with Integrated Electronics for Microchannel-Plate Imaging Detectors", Review of Scientific Instruments, vol. 70, Issue 7, 1999.

Giakos et al., "An Efficient Collector Architecture for Digital Radiographic Imaging CZT Semiconductor Sensors", Proceedings of the 20th IEEE Instrumentation and Measurement Technology Conference, (IMTC '03), pp. 541-544, May 2003.

Michael et al., "Towards Direct Conversion Detectors for Medical Imaging with X-rays", Nuclear Science Symposium Conference Record, 2008. NSS '08. IEEE, pp. 1527-1535, Oct. 2008.

* cited by examiner

*Primary Examiner* — Anastasia Midkiff
(74) *Attorney, Agent, or Firm* — Dean D. Small; The Small Patent Law Group

(57) ABSTRACT

Detector modules for an imaging system and methods of manufacturing are provided. One detector module includes a substrate, a direct conversion sensor material coupled to the substrate and a flexible interconnect electrically coupled to the direct conversion sensor material and configured to provide readout of electrical signals generated by the direct conversion sensor material. The detector module also includes at least one illumination source for illuminating the direct conversion sensor material.

20 Claims, 6 Drawing Sheets

DETECTOR MODULES FOR IMAGING SYSTEMS AND METHODS OF MANUFACTURING

BACKGROUND

Imaging systems are widely used to capture images of objects. For example, diagnostic images of a person or an animal may be obtained to assist a doctor or other health care professional in making an accurate diagnosis. Another example includes imaging luggage, shipping containers, and/or the like for security and/or industrial inspection applications. Imaging systems often include an energy source and one or more detectors. In particular, energy, for example x-rays, produced by the source travel through the object being imaged and are detected by the detectors. In response thereto, the detectors produce analog electrical signals that represents the sensed energy. The analog data received from the detector(s) is then converted to digital signals for subsequent processing and image reconstruction.

Some imaging systems, such as some computed tomography (CT) imaging systems use direct conversion materials, such as semiconductor materials for the detection of x-rays. For example, these direct conversion materials may operate in a count mode wherein counts are detected based on photons impinging on a detecting surface of the conversion material and absorbed therein that also satisfy certain conditions. For example, x-ray photon energy is converted into electron-hole pairs and the resulting current pulse signals are detected and counted when the pulses satisfy certain conditions. The photon counts received at various locations and views are then used by the system to reconstruct an image of an object. However, in conventional CT detector modules using direct conversion materials, some charge generated by x-rays absorbed within the material can get trapped resulting in less accuracy in the counts from subsequent x-rays. This inaccuracy in counts can adversely affect subsequent image reconstruction using this count information. The problem can be particularly acute at higher count rates where the magnitude of charge generation is larger with the probability of trapping events being proportional to the amount of charge.

BRIEF DESCRIPTION

In one embodiment, a detector module is provided that includes a substrate, a direct conversion sensor material coupled to the substrate and a flexible interconnect electrically coupled to the direct conversion sensor material and configured to provide readout of electrical signals generated by the direct conversion sensor material. The detector module also includes at least one illumination source for illuminating the direct conversion sensor material.

In another embodiment, an imaging system is provided that includes an x-ray source for generating x-rays and a detector module for detecting x-rays generated by the x-ray source after passing through an object. The detector module includes detector elements formed from a direct conversion sensor material and having at least one illumination source for illuminating the direct conversion sensor material. The direct conversion sensor material generates analog electrical signals in response to received x-rays and the detector module converts the analog signals to digital signals. The imaging system also includes a processor for reconstructing an image of the object using the digital signals.

In yet another embodiment, a method for manufacturing a detector module is provided. The method includes coupling a direct conversion sensor material to at least one of processing or communication circuitry and providing at least one illumination source to illuminate the direct conversion sensor material. The method also includes providing at least one of a support or thermal stabilization coupled to the direct conversion sensor material to form the detector module.

DETAILED DESCRIPTION

Figure 1:
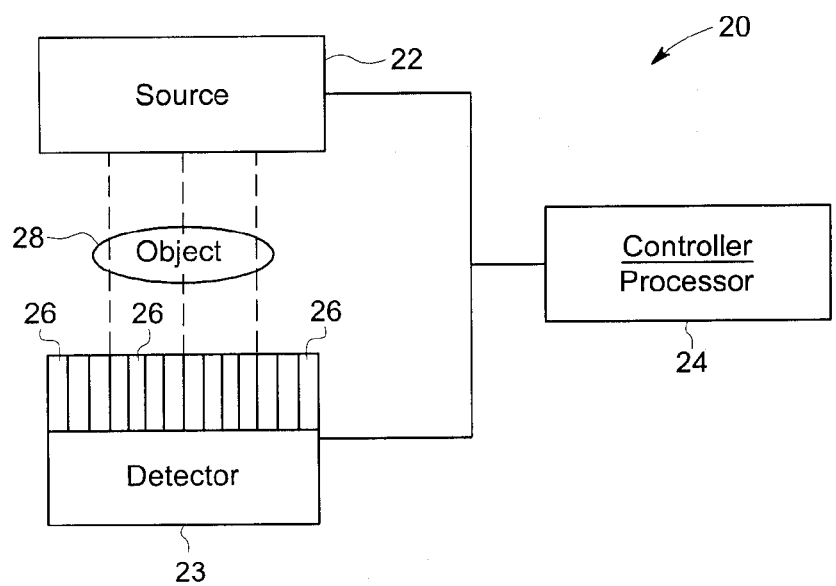
FIG. 1 is a simplified schematic block diagram of an exemplary embodiment of an imaging system.

The following detailed description of certain embodiments will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

Also as used herein, the term "reconstructing" or "rendering" an image or data set is not intended to exclude embodiments in which data representing an image is generated, but a viewable image is not. Therefore, as used herein the term "image" broadly refers to both viewable images and data representing a viewable image. However, many embodiments generate, or are configured to generate, at least one viewable image. In an exemplary embodiment, the "object" being imaged is a human individual. However, the object may alternatively be of another living creature besides a human individual. Moreover, the object is not limited to living creatures, but rather may be of inanimate objects, such as, but not limited to, luggage, shipping containers, and/or the like.

Various embodiments provide imaging detector modules formed from direct conversion materials that have different illumination configurations. Additionally, different support and thermal stabilization configurations are provided. For example, various embodiments provide detector modules formed from direct conversion materials that include anode or cathode illumination (wherein the illumination is different and/or distinct from x-ray illumination). By practicing at least one embodiment, improved mechanical and thermal stability with direct conversion detector materials having a more stable output count rate response that can support accurate count information for imaging at a higher input x-ray flux rate are provided.

The various embodiments may be implemented within imaging systems, which are described herein in connection with computed tomography (CT) systems. However, the various embodiments may be implemented in connection with different types of imaging systems, such as bone-mineral densitometry systems, mammographic screening systems, positron emission tomography (PET) systems and nuclear medicine systems, such as single-photon emission computed tomography (SPECT) systems, as well as other types of imaging systems. Applications of image systems include medical applications, security applications, industrial inspection applications, and/or the like. Thus, although embodiments are described and illustrated herein with respect to a CT imaging system having detectors that detect x-rays, the various embodiments may be used with any other imaging modalities and may be used to detect any other type of electromagnetic energy. Moreover, the various embodiments described and/or illustrated herein are applicable with single slice and/or multi-slice configured systems.

Referring now to FIG. 1, an imaging system 20 generally includes a source 22 of electromagnetic energy, one or more detectors 23, and a controller/processor 24. The detector 23 includes a plurality of detector modules 26 that include detectors (or sensors) formed from a direct conversion material (e.g., Cadmium Telluride (CdTe) or Cadmium Zinc Telluride, also referred to as CdZnTe or CZT) that are illuminated as described in more detail herein. It should be noted that as used herein, a direct conversion detector material generally refers to any detector material that directly converts (in a single conversion step) photons or other high frequency gamma ray energy to electrical signals instead of in a multi-step process such as when using a scintillator (e.g., NaI:Tl (thallium-doped sodium iodide)) and a photo-conversion device (e.g., a photodiode).

Figure 2:
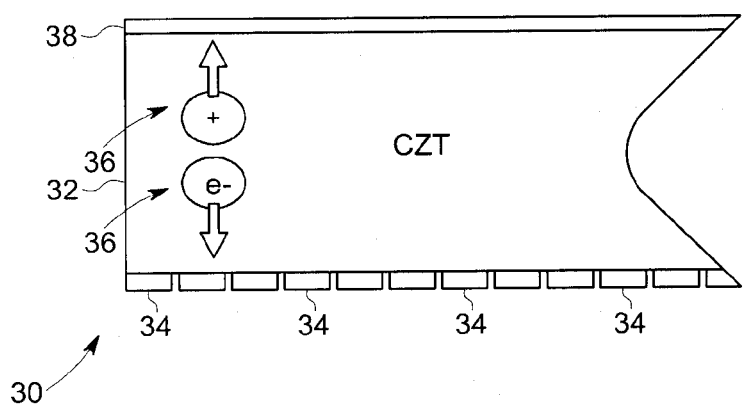
FIG. 2 is a simplified cross-sectional view of a portion of a pixelated detector.

One or more of the detectors 23 may be, for example, a pixelated detector 30 as shown in FIG. 2, illustrating a simplified cross-sectional elevation view of the pixelated detector 30 formed in accordance with various embodiments. The pixelated detector 30 includes a crystal 32 formed from a radiation responsive semiconductor material, which in various embodiments is a direct conversion material, for example, CZT crystals. A pixelated structure having a plurality of pixels is defined, for example, by photolithography or by cutting or dicing of the contact metal on one surface or side of the crystal 32 to form a plurality of pixel electrodes, identified as anodes 34. In operation, a charge in the pixel electrodes, namely the anodes 34 is induced from a large number of electron-hole pairs 36 generated from a detected photon that is absorbed in the crystal 32.

The pixelated detector 30 also includes a cathode 38 on an opposite surface or side of the crystal 32 from the anodes 34 and which may be formed from a single cathode electrode. It should be noted that the anodes 34 generally define the pixels. It also should be noted that one or more collimators may be provided in front of a radiation detecting surface defined by the cathode 38.

Referring again to FIG. 1, the controller/processor 24 may provide power and/or timing signals to the source 22. The controller/processor 24 in various embodiments also schedules calibration and object-image-acquisition phases for operation of the imaging system 20. The detector 23, and in particular the detector modules 26, sense energy emitted by the source 22 that has passed through an object 28 being imaged. In response thereto, the detector 23 produces analog electrical signals that represent the sensed energy. The analog data received from the detector 23 is sampled and converted to digital signals using any suitable analog to digital conversion process. For example, in one embodiment, the detector modules 26 operate in a photon counting mode wherein x-ray photon energy emitted by the source 22 and passing through the object 28 is converted into current pulse signals, which are detected by the detector modules 26. It should be noted that in some embodiments the current pulse signals are integrated over a predetermined time period, then measured and digitized.

The controller/processor 24 performs subsequent processing and image reconstruction using the digital signals. The controller/processor 24 combines data from a calibration operation mode and an object-image-acquisition mode to produce accurate count data that in various embodiments is sufficient for artifact-free or artifact-reduced image reconstruction of the object 28. The reconstructed image(s) may be stored and/or displayed by the controller/processor 24 and/or another device.

Figure 3:
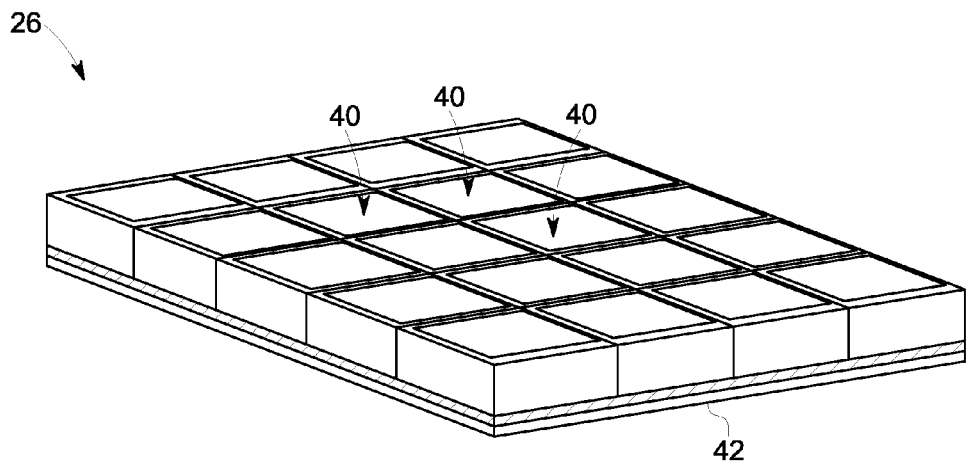
FIG. 3 is a perspective view of a portion of a detector module formed in accordance with an embodiment.

In various embodiments, a plurality of sensor tiles 40 formed from a direct conversion material may be combined to form detector modules 26 as shown in FIG. 3 (illustrating one detector module 26). For example, the detector modules 26 may be configured as a rectangular gamma camera module that includes a plurality, for example, twenty sensor tiles 40 arranged to form a rectangular array of five rows of four sensor tiles 40. The sensor tiles 40 are shown mounted on a substrate 42 that is coupled to processing and/or communication circuitry as described in more detail below. It should be noted that detector modules 26 having larger or smaller arrays of sensor tiles 40 may be provided. Thus, in operation, the energy of a photon detected by the sensor tiles 40 is generally determined from an estimate of the total number of electron-hole pairs produced in a crystal forming the sensor tiles 40 when the photon interacts with the material of the crystal. This count is generally determined from the number of electrons produced in the ionizing event, which is estimated from the charge collected on the anode of the sensor tiles 40.

Various embodiments of detector modules 26 will now be described having different configurations. It should be noted that although the detector modules 26 are described as being configured as CT modules; the detector modules 26 may be used in applications other than CT.

Figure 4:
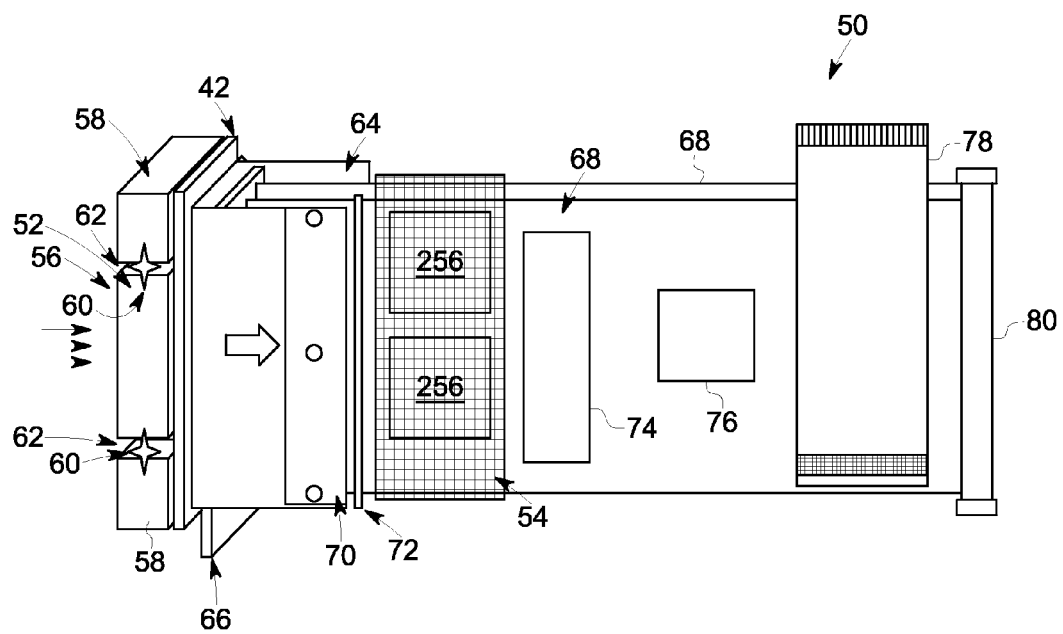
FIG. 4 is a diagram illustrating a detector module formed in accordance with an embodiment providing illumination.

FIG. 4 is one embodiment of a detector module 50 that includes cathode side (also referred to as a common electrode side) illumination of a sensor material, which in one embodiment is a direct conversion material crystal 52 (e.g., CdTe or CZT), which may include a plurality of sensor tiles 40 (e.g., a 32 by 32 array of sensor tiles 40). Thus, a direct conversion sensor is provided as described in more detail herein. The crystal 52 is mounted to the substrate 42, for example, using a suitable epoxy or adhesive. In one embodiment, the substrate 42 is formed from a multi-layer ceramic (MLC) material, such as aluminum nitride (AlN), aluminum oxide (Al2O3) or a high density silicon or glass substrate. However, it should be noted that any suitable support material may be used that provides support of the crystal 52 within the detector module 50, such as during rotation of a CT imaging system in which the detector module 50 is installed.

It also should be noted that the substrate 42 also allows for the electrical connection of the crystal 52 to processing and/or communication circuitry that generally reads out the electrical pulse signals generated by the crystal 52. For example, in one embodiment, the substrate 42 includes copper traces and/or metal vias therethrough to provide the electrical connection through the substrate 42. The electrical connections provide a signal path from the crystal 52 to one or more application application-specific integrated circuit (ASIC) 54 and/or other processing and/or communication circuitry. For example, the ASIC 54 and/or the processing and/or communication circuitry may receive the electrical pulse signals from the crystal 52 and read out the signals from the crystal 52, as well as digitize the electrical signals, which are analog signals. It should be noted that although two 256 channel ASICs 54 are shown, additional or fewer ASICs 54 with additional or fewer channels may be provided. It also should be noted that the ASICs 54 may include suitable heat sinks and may be embodied as part of an ASIC board having the ASICs 54 thereon. For example, the ASIC board may be configured as a current module that converts the received analog signals to digital signals using any suitable conversion process.

Thus, the ASIC 54 in various embodiments is configured to operate as readout electronic circuitry. For example, a high voltage surface 56 (e.g., a sensing or detection face) of the crystal 52, which in this embodiment, is the cathode side of the crystal 52, has a high voltage applied thereto. For example, a high voltage may be applied such that about 1000 volts is generated between the cathode side (common contact) and the opposite anode side, which includes a pixelated structure that is effectively grounded. In one embodiment the crystal 52 is configured similar to the pixelated detector 30 (shown in FIG. 2) having the cathode 38 (which includes the high voltage surface 56) on an opposite surface or side of the substrate (illustrated as the crystal 52 in FIG. 4) from the anodes 34 and which may be formed from a single cathode electrode. In various embodiments, the anode side, and in particular, the anode pixels are connected directly to the substrate 42, for example, to the vias of the substrate using a suitable conductive material, such as metal, solder (e.g., solder bumps or balls) or conductive adhesive (e.g., epoxy plus a filler, such as nickel or graphite), among others.

In some embodiments, one or more spacers 58 may be mounted to the substrate 42 adjacent the crystal 52. For example, in one embodiment, a spacer 58 is mounted on each side of the crystal 52 with a gap therebetween. The spacers 58 may be sized and shaped as desired or needed. The spacers 58 may be mounted to the substrate 42 such that the spacers 58 occupy the remaining surface area or space of the substrate 42 (other than the gap between the spacers 58 and the crystal 52). Thus, in one embodiment, the spacers 58 extend from a distance apart from the crystal 52 to the edges of the substrate 42.

The detection end of the detector module 50 (where, for example, x-rays or gamma rays impinge as illustrated by the arrows), which generally includes the crystal 52 mounted to the substrate 42 (and having the optional spacers 58) also includes one or more illumination sources 60. In the illustrated embodiment, an illumination source 60 is provided on each side of the crystal 52. The illumination sources 60 may be coupled to the detection end in different ways. For example, in one embodiment, the illumination sources 60 are embedded in the spacers 58 or in the substrate 42 in the gap between the spacers 58 and the crystal 52. In another embodiment, the illumination sources 60 are coupled to a surface of the spacers 58 or the substrate 42, such as by using a suitable glue or epoxy (or other suitable fastening means).

The illumination sources 60 may be any device capable of illuminating the crystal 52, which in this embodiment illuminates the cathode side of the crystal 52. The illumination source 60 may be powered alternately on and off by the controller 24 in coordination with the operation of the source 22 so as to support more stable and accurate count data by elimination of trapped charge. For example, the illumination sources 60 may provide optical or infrared (IR) illumination of the cathode side of the crystal 52. The illumination sources 60 may be, for example, a single light emitting diode (LED) or an array of LEDs, such as one or more IR LEDs or optical LEDs. As other examples, the illumination sources 60 may be lamps or laser diodes. In some embodiments, the illumination sources 60 generate signals that are not in the visible optical spectrum. For example, the illumination sources 60 may be near-field or mid-field IR LEDs. In general, the illumination sources 60 are configured to generate illumination of sufficiently long wavelength that is insufficient to create an electron-hole pair such that a charge is not created in the crystal 52 (such as when an x-ray or gamma ray impinges on the crystal 52). The wavelength is configured of sufficiently short wavelength to create detrapping of trapped charge. For example, for CZT and CdTe, in one embodiment, the wavelength of illumination source 60 is greater than about 0.9 but less than 25 microns. However, other wavelengths may be used as desired or needed.

It should be noted that in the illustrated embodiment, the illumination by the illumination sources 60 is provided from or at the perimeter sidewall area 62 of the crystal 52. However, the illumination by the illumination sources 60 may be provided at different locations or by different means. For example, in one embodiment, the illumination sources 60 are provided such that the illumination is through the cathode or anode contacts, which may be fabricated from a transparent conductor material, for example, a transparent conducting oxide such as indium tin oxide (ITO). Thus, the illumination sources 60 may be mounted below the crystal 52 between the crystal 52 and the substrate 42. In further embodiments, the illumination sources 60 may be mounted in more remote locations and the light from the illumination sources directed to the crystal 52 by means of a optical coupler. The optical couplers can be fabricated from, for example, fiber optics or sheet optics.

The illumination of the crystal 52 in some embodiments operates to un-trap or release charges trapped in the crystal 52. Thus, the illumination of the crystal 52 in some embodiments provides more repeatable operation and allows more accurate photon counts to be detected by the detector module 50. It should be noted that the illumination may also be chosen or selected to purposely create some electron-hole pairs in some embodiments so as to provide for real-time calibration of the detector module 50. For example, the output of the detector module 50 for an x-ray signal may be scaled by the response of the detector module 50 for the signal from the illumination sources 60. In particular, a pulsed illumination source created from a laser diode can provide a fast charge pulse in the crystal 52 that mimics (or imitates, copies or approximates) that created by an X-ray or gamma-ray absorbed in the crystal 52. For example, in one embodiment, the current pulse of such a mimicked signal has a temporal period of between about 1 to 1000 nanoseconds and an amplitude of between about 0.02 to 20 microamps. Such calibration operation in relation to the object image acquisition is supported by the coordinating function of the controller 24. However, other calibration sources may be used, such as a radioactive source in the same locations as the illumination sources 60.

In the illustrated embodiment, the direct conversion sensor arrangement on the detection end of the detector module 50 is coupled to the ASIC 54 in a generally perpendicular arrangement. However, other orientations are contemplated.

In particular, the crystal 52 is electrically connected to one side of the substrate 42 and the processing and/or communication circuitry, which may be embodied in or provided as part of one or more readout boards 68 (that include the ASICs 54), is electrically connected to the other side of the substrate 42. The readout boards 68 may be, for example, printed circuit boards (PCBs) configured as analog readout boards.

The electrical connection may be provided from traces on both sides of the substrate 42 through the vias. Accordingly, the current signals from the crystal 52 flow through the substrate 42 to the processing and/or communication circuitry, in particular, to a flexible interconnect 64 coupled to the substrate 42, such as using a suitable conductive epoxy. The flexible interconnect 64 may be any type of flexible interconnect device, such as a flexible PCB. For example, in one embodiment, the flexible interconnect 64 is an analog flexible PCB that defines a routing density consistent with a plurality of readout channels (e.g., 512 channels). It should be noted that although the flexible interconnect 64 is shown in FIG. 4 having a generally "U" shaped configuration, other configurations are contemplated, such as an "L" shaped configuration or a "T" shaped configuration. Additionally, one or more clamps 70 may be provided on each end of the flexible interconnect 64, which may be used to connect the ends to the readout boards 68. However, other fastening arrangements are contemplated. For example, solder, conductive epoxy or demountable electronic connector means may be used.

A support member 66 also may be provided, such as a metal (e.g., aluminum) support bar. The support member 66 provides positioning of, mechanically supporting, and/or thermally stabilizing the substrate 42. The support member 66 can contain or support, for example, thermal heater and temperature sensors to allow active temperature control. The support member 66 is coupled to the flexible interconnect 64 opposite the substrate 42 such that a portion of the flexible interconnect 64 is sandwiched therebetween. For example, the support member 66 extends between the legs of the "U" shape of the flexible interconnect 64 to provide mechanical support for the connection of the traces of the flexible interconnect 64 to the traces of the substrate 42.

Additionally, one or more clamps may be provided on each end of the support member 66, which may be used to connect the ends to a housing (not shown) and thereby position the detector module 50 (illustrated as 24 in FIG. 1) on the detector 23. However, other fastening arrangements are contemplated. For example, solder, pins or another mechanical fastening means may be used.

The detector module 50 also optionally may include a light seal 72, which may be any suitable light blocking device. For example, the light seal 72 may be positioned adjacent the ends of the flexible interconnect 64 to prevent or reduce the likelihood of light passing to the detection end of the detector module 50, which may include light sensitive devices (e.g., photodiodes or semiconductors).

The one or more readout boards 68 also include a power regulator 74 for regulating power to the one or more readout boards 68 and the components of the detector module 50. The power regulator 74 may be any type of power regulation device, such as a constant power source to power, for example, the ASICs 54.

Additionally, the one or more readout boards 68 include a controller 76, which is illustrated as a field-programmable gate array (FPGA). The controller 76 in various embodiments provides digital signaling to coordinate the operation of the various components of the one or more readout boards 68, such as to readout the digitized signals from the ASICs 54 and operation of the illumination source 60 in respective calibration and acquisition modes. The controller 76 may be programmed in different ways to respond to the controller/processor 24, for example, and based on the signals to be received, the number of channels, and/or the system in which the detector module 50 is to be installed, among others. For example, the controller 76 can combine calibration and acquisition data with a suitable algorithm to generate accurate count data. Additionally, the controller 76 may control the output of the digitized signals from the detector module 50 to a CT processing system that uses the signals to reconstruct an image. The connection of the detector module 50 to the system to allow the output of the digitized signals may be provided, for example, using a connector 78, which is illustrated as a ribbon connector with electrical traces for outputting the digitized signals.

The detector module 50 also includes a mechanical interface 80 at a connection end of the detector module 50 opposite the detection end. The mechanical interface 80 may be, for example, a card cage mechanical interface that allows the detector module 50 to be connected to a system (e.g., the CT system).

In the various embodiments, the Y direction is generally along the direction of the source 22, for example, an x-ray source of a CT system. The Z direction is along an examination axis, for example, along a body of a patient being imaged (e.g., from head to toe in a CT scan) or the belt-axis of a baggage scanning system and the X direction is transverse to the examination axis.

Figure 5:
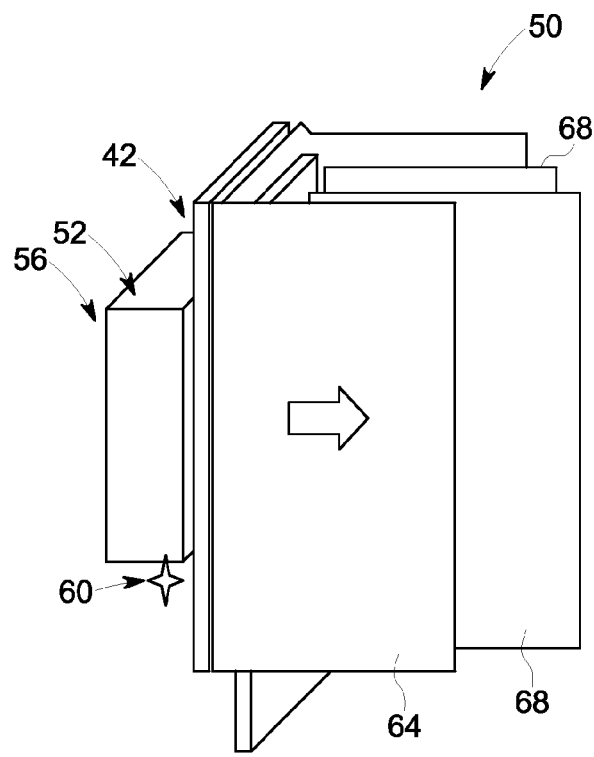
FIG. 5 is a diagram illustrating a portion of a detector module formed in accordance with another embodiment providing illumination.
Figure 6:
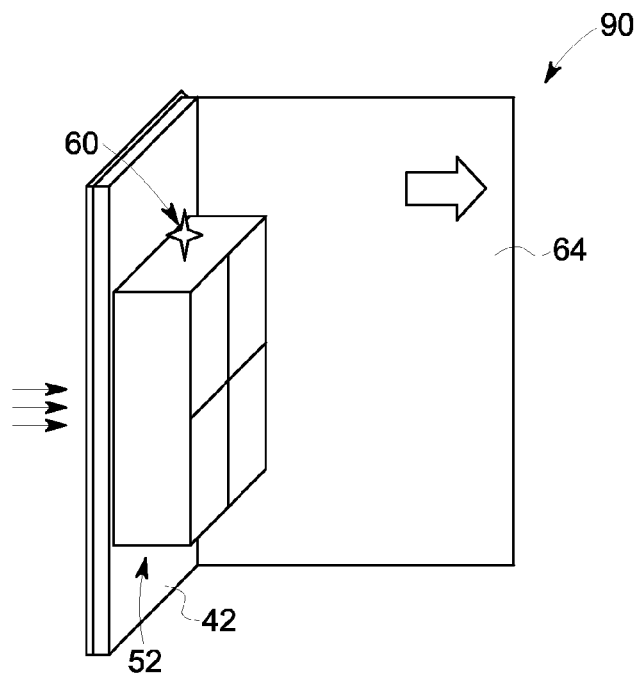
FIG. 6 is a diagram illustrating a portion of a detector module formed in accordance with another embodiment providing illumination.
Figure 7:
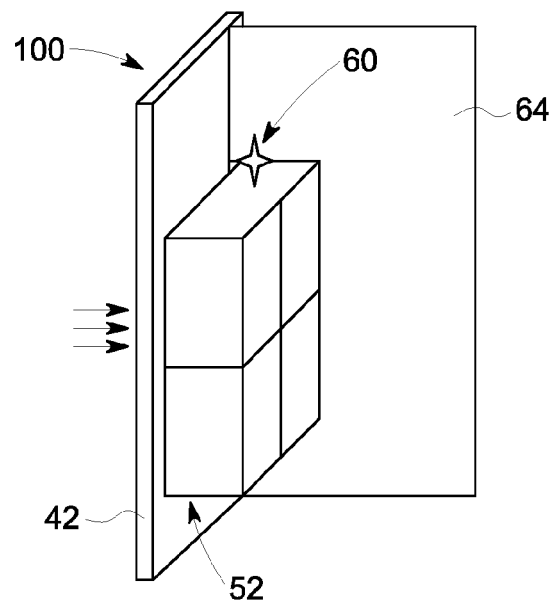
FIG. 7 is a diagram illustrating a portion of a detector module formed in accordance with another embodiment providing illumination.
Figure 8:
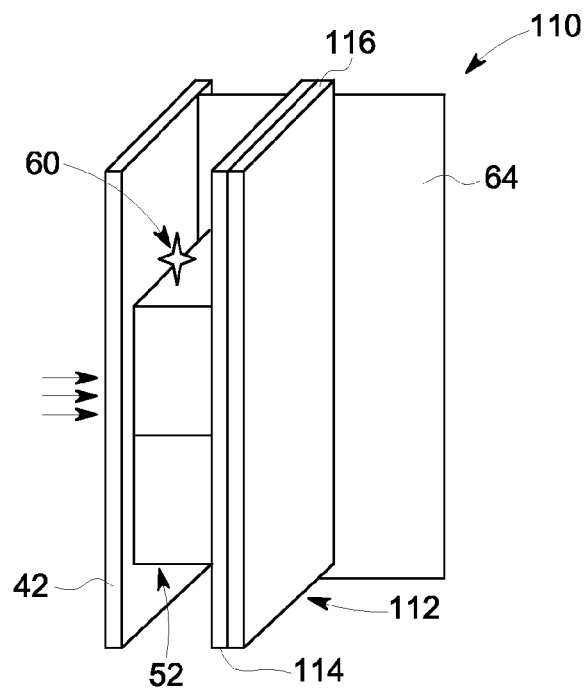
FIG. 8 is a diagram illustrating a portion of a detector module formed in accordance with another embodiment providing illumination.

Variations and modifications are contemplated. For example, as illustrated in FIG. 5, showing a portion of the detector module 50, the spacers 58 may be removed. In other embodiments, for example, as shown in FIGS. 6 through 8 (showing a portion of the detector modules), the illumination sources 60 may be positioned to provide anode side illumination of the crystal 52. It should be noted that like numerals represent like or similar parts throughout the figures.

In particular, as shown in FIG. 6, a detector module 90 is provided that includes anode side illumination of the crystal 52 (e.g., CdTe or CZT), which may include a plurality of sensor tiles 40 (e.g., a 32 by 32 array of sensor tiles 40). In this embodiment, the crystal 52 is mounted to back side of the substrate 42, with the flexible interconnect 64 mounted to a front side of the substrate 42, namely the side having x-rays or gamma rays impinging thereon (as illustrated by the arrows).

In this embodiment, the electron charge generated in the crystal 52 from an impinging x-rays or gamma rays travels from the back (cathode side) of the crystal 52 towards the front (anode side) of the crystal 52. The cathode side is the common electrical side and may be formed, for example, from a metal layer on top of the crystal 52. Accordingly, the signal currents in this embodiment travel from the crystal 52 (opposite the direction of the incoming x-rays or gamma rays) through the substrate 42 into the flexible interconnect 64. Thus, a portion of the flexible interconnect 64 (that is electrically connected to the crystal 52) is attached to the pixel side of the crystal 52 through the substrate 42 such that the substrate 42 is coupled between the flexible interconnect 64 and the crystal 52.

In this embodiment, the flexible interconnect 64 and the substrate 42 are formed from a low atomic number material (e.g., polymers) and also may be thinner than the flexible interconnect 64 and the substrate 42 shown in FIGS. 4 and 5 to allow, for example, x-rays and gamma rays to pass therethrough without attenuation. The crystal 52 is formed from a high atomic number material (e.g., a semiconductor material).

The flexible interconnect 64 is routed around the crystal 52 is an "L" type configuration such that received signals are routed therethrough and around the crystal 52. As can be seen, the illumination sources 60 again may be mounted or embedded adjacent the crystal 52, which in this embodiment, thereby provide anode side illumination.

It should be appreciated that in FIGS. 5 through 9, one or more readout boards 68, as well as the other components described in connection with FIG. 4 also may be provided.

As another example, and as shown in FIG. 7, anode side illumination is again provided. However, in this embodiment, the detector module 100 includes the flexible interconnect 64 coupled between the substrate 42 and the anode side of the crystal 52. The detector module 100 may be coupled (e.g., bolted), for example, to rails (not shown) of a CT system, by attaching the substrate 42 to the rails. As another example, FIG. 8 shows a detector module 110, similar to the detector module 100 and providing anode side illumination. In this embodiment, additional support is provided such that the crystal 52 is supported on both sides. In particular, a support structure 112 is provided such that the crystal 52 is mounted between the flexible interconnect 64, supported by the substrate 42 on an outside, and the support structure 112 on the opposite side. The support structure 112 in the illustrated embodiments is formed from a substrate 114 (similar to the substrate 42) and having an additional backing layer 116, which may be formed from a material that provides thermal grounding and active temperature control. It should be noted that additional of different supports and/or thermal stabilizations may be provided as desired or needed.

Figure 9:
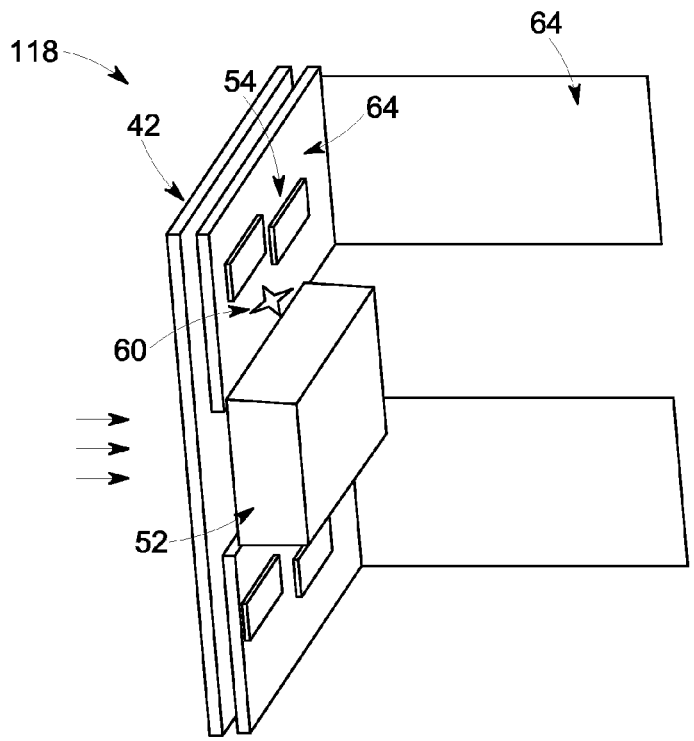
FIG. 9 is a diagram illustrating a portion of a detector module formed in accordance with another embodiment providing illumination.

As still another example, a detector module 118 as shown in FIG. 9, includes ASICs 54 located on the flexible interconnect 64 and further supported mechanically and electrically by the substrate 42. Thus, in this embodiment, the ASICs 54 are mounted to flexible interconnects 64, which are mounted to the substrate 42. Electrical vias through the flexible interconnect 64 connect a high density of analog traces on the substrate 42 from the anodes on the crystal 52 to the ASICs 54. The system digital communication, power and ground interconnects from the ASICs 54 are routed to the readout boards 68 through the flexible interconnect. The crystal 52 is mounted on the substrate 42 between the flexible interconnects 64.

Figure 10:
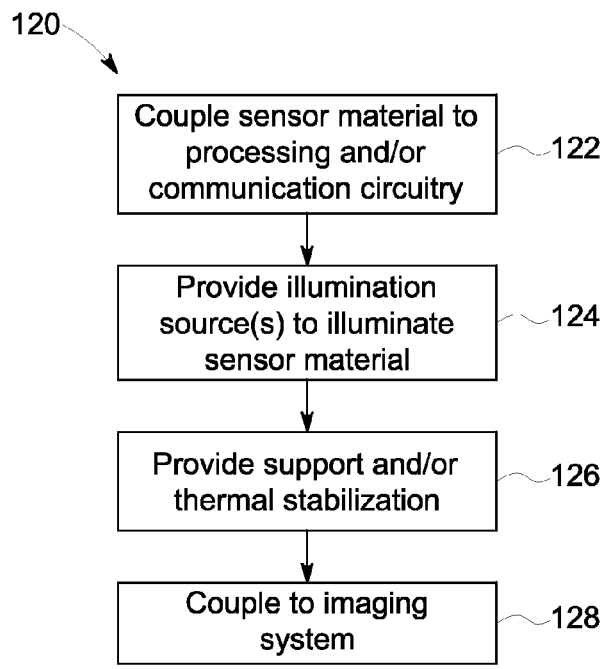
FIG. 10 is a flowchart of a method of manufacturing a detector module in accordance with various embodiments.

Various embodiments also provide a method 120 as shown in FIG. 10 for manufacturing a detector module. The method 120 includes coupling at 122 a sensor material to processing and/or communication circuitry. For example, a direct conversion sensor material that directly converts, for example, x-rays or gamma rays within the material to electrical signals is coupled to analog readout boards through a substrate that provides electrical connection to a flexible interconnect to readout the electrical signals.

The method also includes providing illumination source(s) at 124 for illuminating the sensor material. As described herein, the illumination may be cathode side illumination and/or an anode side illumination. Supports and or thermal stabilizers also may be provided at 126 as described herein.

The components that form the detector module are then coupled to an imaging system at 128. For example, the detector module may be mounted to rails of a CT system that allow the detector module to rotate about an object (e.g., a patient).

It should be noted that the various steps of the method 120 may be performed in any order and more than one time.

Figure 11:
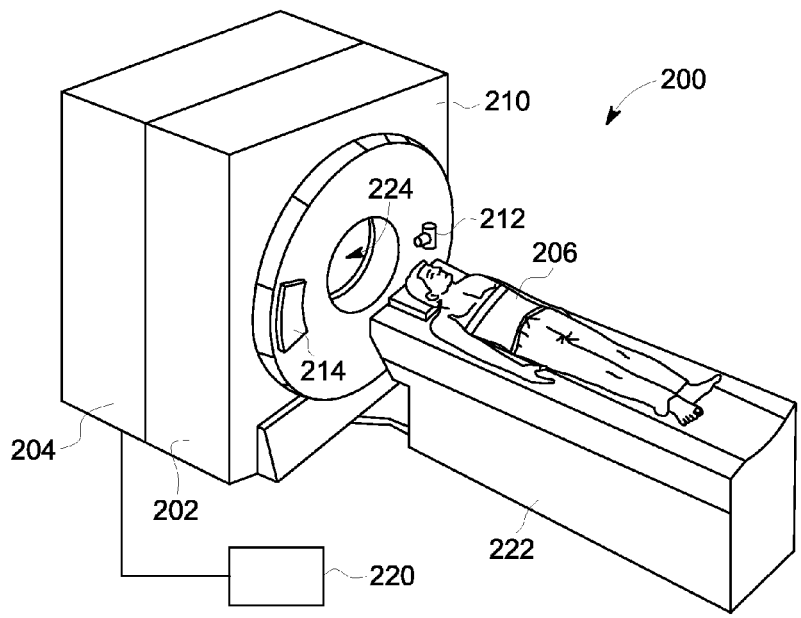
FIG. 11 is a pictorial drawing of an exemplary embodiment of an imaging system in which a detector module of various embodiments may be implemented.
Figure 12:
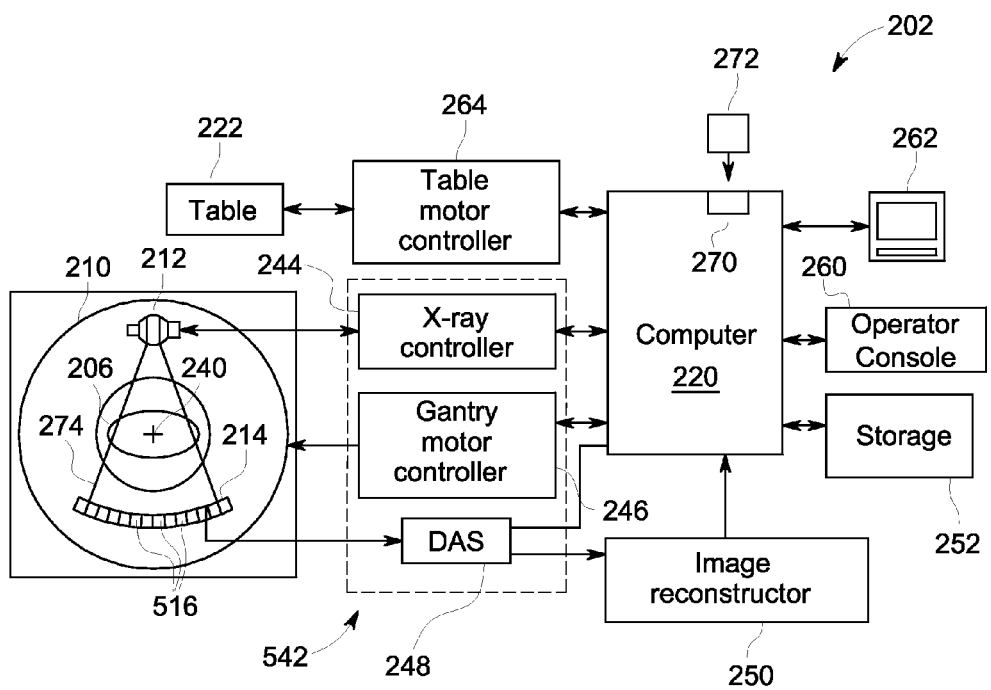
FIG. 12 is a schematic block diagram of the imaging system shown in FIG. 11.

The various embodiments may be implemented in connection with different types of imaging systems. For example, FIG. 11 is a pictorial view of an exemplary imaging system 200 that is formed in accordance with various embodiments. FIG. 12 is a block schematic diagram of a portion of the imaging system 200 shown in FIG. 11. Although various embodiments are described in the context of an exemplary dual modality imaging system that includes a computed tomography (CT) imaging system and a positron emission tomography (PET) imaging system, it should be understood that other imaging systems capable of performing the functions described herein are contemplated as being used, including single modality imaging systems.

The multi-modality imaging system 200 is illustrated, and includes a CT imaging system 202 and a PET imaging system 204. The imaging system 200 allows for multiple scans in different modalities to facilitate an increased diagnostic capability over single modality systems. In one embodiment, the exemplary multi-modality imaging system 200 is a CT/PET imaging system 200. Optionally, modalities other than CT and PET are employed with the imaging system 200. For example, the imaging system 200 may be a standalone CT imaging system, a standalone PET imaging system, a magnetic resonance imaging (MRI) system, an ultrasound imaging system, an x-ray imaging system, and/or a single photon emission computed tomography (SPECT) imaging system, interventional C-Arm tomography, CT systems for a dedicated purpose such as extremity or breast scanning, and combinations thereof, among others.

The CT imaging system 202 includes a gantry 210 that has an x-ray source 212 that projects a beam of x-rays toward a detector array 214 on the opposite side of the gantry 210. The detector array 214 includes a plurality of detector elements 516 that are arranged in rows and channels that together sense the projected x-rays that pass through an object, such as the subject 206, and which may be configured as a detector module according to one or more embodiments described herein. The imaging system 200 also includes a computer 220 that receives the projection data from the detector array 214 and processes the projection data to reconstruct an image of the subject 206. In operation, operator supplied commands and parameters are used by the computer 220 to provide control signals and information to reposition a motorized table 222. More specifically, the motorized table 222 is utilized to move the subject 206 into and out of the gantry 210. Particularly, the table 222 moves at least a portion of the subject 206 through a gantry opening 224 that extends through the gantry 210.

As discussed above, the detector 214 includes a plurality of detector elements 516. Each detector element 516 produces an electrical signal, or output, that represents the intensity of an impinging x-ray beam and hence allows estimation of the attenuation of the beam as it passes through the subject 206. During a scan to acquire the x-ray projection data, the gantry 210 and the components mounted thereon rotate about a center of rotation 240. FIG. 12 shows only a single row of detector elements 516 (i.e., a detector row). However, the multislice detector array 214 includes a plurality of parallel detector rows of detector elements 516 such that projection data corresponding to a plurality of slices can be acquired simultaneously during a scan.

Rotation of the gantry 210 and the operation of the x-ray source 212 are governed by a control mechanism 542. The control mechanism 542 includes an x-ray controller 244 that provides power and timing signals to the x-ray source 212 and a gantry motor controller 246 that controls the rotational speed and position of the gantry 210. A data acquisition system (DAS) 248 in the control mechanism 542 samples analog data from detector elements 516 and converts the data to digital signals for subsequent processing. Thus, the DAS 248 may be embodied as the more readout boards 68. An image reconstructor 250 receives the sampled and digitized x-ray data from the DAS 248 and performs high-speed image reconstruction. The reconstructed images are input to the computer 220 that stores the image in a storage device 252. Optionally, the computer 220 may receive the sampled and digitized x-ray data from the DAS 248. The computer 220 also receives commands and scanning parameters from an operator via a console 260 that has a keyboard. An associated visual display unit 262 allows the operator to observe the reconstructed image and other data from computer.

The operator supplied commands and parameters are used by the computer 220 to provide control signals and information to the DAS 248, the x-ray controller 244 and the gantry motor controller 246. In addition, the computer 220 operates a table motor controller 264 that controls the motorized table 222 to position the subject 206 in the gantry 210. Particularly, the table 222 moves at least a portion of the subject 206 through the gantry opening 224 as shown in FIG. 11.

Referring again to FIG. 12, in one embodiment, the computer 220 includes a device 270, for example, a floppy disk drive, CD-ROM drive, DVD drive, magnetic optical disk (MOD) device, or any other digital device including a network connecting device such as an Ethernet device for reading instructions and/or data from a computer-readable medium 272, such as a floppy disk, a CD-ROM, a DVD or an other digital source such as a network or the Internet, as well as yet to be developed digital means. In another embodiment, the computer 220 executes instructions stored in firmware (not shown). The computer 220 is programmed to perform functions described herein, and as used herein, the term computer is not limited to just those integrated circuits referred to in the art as computers, but broadly refers to computers, processors, microcontrollers, microcomputers, programmable logic controllers, application specific integrated circuits, and other programmable circuits, and these terms are used interchangeably herein.

In the exemplary embodiment, the x-ray source 212 and the detector array 214 are rotated with the gantry 210 within the imaging plane and around the subject 206 to be imaged such that the angle at which an x-ray beam 274 intersects the subject 206 constantly changes. A group of x-ray attenuation measurements, i.e., projection data, from the detector array 214 at one gantry angle is referred to as a "view". A "scan" of the subject 206 comprises a set of views made at different gantry angles, or view angles, during one revolution of the x-ray source 212 and the detector 214. In a CT scan, the projection data is processed to reconstruct an image that corresponds to a two dimensional slice taken through the subject 206.

Exemplary embodiments of a multi-modality imaging system are described above in detail. The multi-modality imaging system components illustrated are not limited to the specific embodiments described herein, but rather, components of each multi-modality imaging system may be utilized independently and separately from other components described herein. For example, the multi-modality imaging system components described above may also be used in combination with other imaging systems.

The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a floppy disk drive, optical disk drive, and the like. The storage device may also be other similar means for loading computer programs or other instructions into the computer or processor.

As used herein, the term "computer" or "module" may include any processor-based or microprocessor-based system including systems using microcontrollers, Reduced Instruction Set Computers (RISC), ASICs, logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments. The set of instructions may be in the form of a software program, which may form part of a tangible non-transitory computer readable medium or media. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments without departing from their scope. While the dimensions and types of materials described herein are intended to define the parameters of the various embodiments, the embodiments are by no means limiting and are exemplary embodiments. Many other embodiments will be apparent to those of skill in the art upon reviewing the above description. The scope of the various embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the various embodiments, including the best mode, and also to enable any person skilled in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal languages of the claims.

What is claimed is:

1. A detector module comprising:
   a substrate;
   a direct conversion sensor material coupled to the substrate;
   a flexible interconnect electrically coupled to the direct conversion sensor material and configured to provide readout of electrical signals generated by the direct conversion sensor material; and
   at least one illumination source for illuminating the direct conversion sensor material, wherein the illumination source is one of coupled or embedded in the substrate.

2. The detector module of claim 1, wherein the illumination source is configured to illuminate a cathode side of the direct conversion sensor material.

3. The detector module of claim 1, wherein the illumination source is configured to illuminate an anode side of the direct conversion sensor material.

4. The detector module of claim 1, wherein the substrate is coupled between the direct conversion sensor material and the flexible interconnect.

5. The detector module of claim 4, wherein an anode side of the direct conversion sensor material is coupled to the substrate.

6. The detector module of claim 5, wherein the flexible interconnect is coupled between the substrate and one or more application application-specific integrated circuits (ASICs).

7. The detector module of claim 4, wherein a cathode side of the direct conversion sensor material is coupled to the substrate.

8. The detector module of claim 1, wherein the flexible interconnect is coupled between the substrate and the direct conversion sensor material.

9. The detector module of claim 8, wherein a support structure is coupled to the direct conversion sensor material on an opposite side to the flexible interconnect.

10. The detector module of claim 1, further comprising spacers coupled to the substrate and having gaps therebetween and wherein the illumination source is coupled to or embedded in the substrate in the gaps.

11. The detector module of claim 1, wherein the illumination source is configured to illuminate a perimeter sidewall area of the direct conversion sensor material.

12. The detector module of claim 1, wherein the direct conversion sensor material comprises one of Cadmium Telluride (CdTe) or Cadmium Zinc Telluride (CZT).

13. The detector module of claim 1, wherein the direct conversion sensor material is configured to detect one of x-rays or gamma rays.

14. An imaging system comprising:
   an x-ray source for generating x-rays;
   a detector module for detecting x-rays generated by the x-ray source after passing through an object, the detector module having detector elements formed from a direct conversion sensor material and having at least one illumination source for illuminating the direct conversion sensor material, the direct conversion sensor material generating analog electrical signals in response to received x-rays, the detector module converting the analog signals to digital signals, wherein the illumination source is pulsed to mimic absorbed x-rays or gamma-rays received by the direct conversion sensor material; and
   a processor for reconstructing an image of the object using the digital signals.

15. The imaging system of claim 14, wherein the detector module further comprises a flexible interconnect electrically coupled to the direct conversion sensor material and configured to provide readout of the analog electrical signals generated by the direct conversion sensor material.

16. The imaging system of claim 14, wherein the illumination source is configured by the processor to provide real time calibration of the response of the detector module.

17. The imaging system of claim 14, wherein the illumination source is pulsed to have a temporal period of between about 1 to 1000 nanoseconds and an amplitude of between about 0.02 to 20 microamps.

18. The imaging system of claim 14, wherein the illumination source is configured to illuminate a perimeter sidewall area of the direct conversion sensor material.

19. A method for manufacturing a detector module, the method comprising:
   coupling a direct conversion sensor material to at least one of processing or communication circuitry;
   providing at least one illumination source at a perimeter sidewall area of the direct conversion sensor material to illuminate the direct conversion sensor material; and
   providing at least one of a support or thermal stabilization coupled to the direct conversion sensor material to form the detector module.

20. The method of claim 19, further comprising coupling the detector module to an imaging system.

* * * * *